United States Patent
Hok et al.

(10) Patent No.: US 10,151,744 B2
(45) Date of Patent: Dec. 11, 2018

(54) HIGHLY ACCURATE BREATH TEST SYSTEM

(71) Applicant: Automotive Coalition for Traffic Safety, Inc., Washington, DC (US)

(72) Inventors: Bertil Hok, Vasteras (SE); Leif Smith, Uppsala (SE); Mathias Granstam, Vasteras (SE)

(73) Assignee: Automotive Coalition for Traffic Safety, Inc., Washington, DC (US)

( * ) Notice: Subject to any disclaimer, the term of this patent is extended or adjusted under 35 U.S.C. 154(b) by 0 days.

(21) Appl. No.: 14/421,376

(22) PCT Filed: Aug. 23, 2013

(86) PCT No.: PCT/SE2013/050990
§ 371 (c)(1),
(2) Date: Feb. 12, 2015

(87) PCT Pub. No.: WO2014/031071
PCT Pub. Date: Feb. 27, 2014

(65) Prior Publication Data
US 2015/0233897 A1    Aug. 20, 2015

(30) Foreign Application Priority Data
Aug. 24, 2012  (SE) ..................... 1250953

(51) Int. Cl.
*G01N 33/497* (2006.01)
*G01N 21/3504* (2014.01)
(Continued)

(52) U.S. Cl.
CPC ......... *G01N 33/4972* (2013.01); *A61B 5/082* (2013.01); *A61B 5/087* (2013.01);
(Continued)

(58) Field of Classification Search
CPC ............ G01N 33/497; G01N 33/4972; G01N 2033/4975
See application file for complete search history.

(56) References Cited

U.S. PATENT DOCUMENTS 3,283,563 A   11/1966   Turner et al.
3,301,482 A   1/1967    Bullen
(Continued)

FOREIGN PATENT DOCUMENTS

CN    1586944    3/2005
CN    101292158  10/2008
(Continued)

OTHER PUBLICATIONS

International Search Report dated Feb. 3, 2014 for PCT/SE2013/050990.
(Continued)

*Primary Examiner* — Justin Seo
*Assistant Examiner* — Alex DeVito
(74) *Attorney, Agent, or Firm* — Pandiscio & Pandiscio

(57) ABSTRACT

The invention relates to a system for breath test of a person. It includes a sensor unit configured to sense the presence/concentration of a volatile substance, e.g. alcohol, present in air flowing through a predefined inlet area and generating a signal corresponding to the concentration of said substance. An analyzer determines the concentration of said substance in the breath of said person. It comprises means for the temporary interruption of said air flow at a point in time coinciding with the detection of a breath. It also relates to a method comprising interrupting the flow through said predefined area for a predetermined period of time, and detecting the concentration of said substance during said interruption.

13 Claims, 3 Drawing Sheets

(51) Int. Cl.
*G01N 15/06* (2006.01)
*A61B 5/08* (2006.01)
*A61B 5/087* (2006.01)
*A61B 5/18* (2006.01)
*A61B 5/00* (2006.01)
*G01N 1/22* (2006.01)
*B60K 28/06* (2006.01)

(52) U.S. Cl.
CPC .............. *A61B 5/18* (2013.01); *A61B 5/4845* (2013.01); *G01N 1/22* (2013.01); *G01N 15/06* (2013.01); *G01N 21/3504* (2013.01); *B60K 28/06* (2013.01); *G01N 2001/2244* (2013.01); *G01N 2015/0693* (2013.01)

(56) References Cited

U.S. PATENT DOCUMENTS

| | | | |
|---|---|---|---|
| 3,792,272 A | 2/1974 | Harte et al. | |
| 3,792,351 A | 2/1974 | Ireland | |
| 3,830,630 A | 8/1974 | Kiefer et al. | |
| 3,897,659 A | 8/1975 | Henry | |
| 4,090,078 A | 5/1978 | Heim | |
| 4,535,620 A | 8/1985 | Cunningham | |
| 4,678,057 A | 7/1987 | Elfman | |
| 4,749,553 A | 6/1988 | Lopez et al. | |
| 4,843,377 A | 6/1989 | Fuller et al. | |
| 4,868,545 A | 9/1989 | Jones | |
| 4,916,435 A | 4/1990 | Fuller et al. | |
| 4,975,581 A | 12/1990 | Robinson et al. | |
| 5,006,315 A | 4/1991 | Maroulis et al. | |
| 5,303,575 A | 4/1994 | Brown et al. | |
| 5,426,415 A | 6/1995 | Prachar et al. | |
| 5,458,853 A | 10/1995 | Porter et al. | |
| 5,544,276 A | 8/1996 | Loux et al. | |
| 5,652,398 A | 7/1997 | Johnson | |
| 5,655,530 A | 8/1997 | Messerschmidt | |
| 5,693,944 A | 12/1997 | Rich | |
| 5,746,973 A | 5/1998 | Naraghi | |
| 5,823,951 A | 10/1998 | Messerschmidt | |
| 5,830,112 A | 11/1998 | Wang et al. | |
| 5,877,345 A | 3/1999 | Bauer et al. | |
| 5,906,203 A * | 5/1999 | Klockseth | A62B 18/006 128/201.25 |
| 5,955,886 A | 9/1999 | Cohen et al. | |
| 5,971,937 A | 10/1999 | Ekstrom | |
| 6,123,674 A | 9/2000 | Rich | |
| 6,129,680 A * | 10/2000 | Mottram | G01N 33/497 422/84 |
| 6,152,876 A | 11/2000 | Robinson et al. | |
| 6,157,041 A | 12/2000 | Thomas et al. | |
| 6,229,908 B1 | 5/2001 | Edmonds et al. | |
| 6,266,353 B1 | 7/2001 | Freitas et al. | |
| 6,441,388 B1 | 8/2002 | Thomas et al. | |
| 6,468,222 B1 | 10/2002 | Mault et al. | |
| 6,488,635 B1 | 12/2002 | Mottrarn | |
| 6,528,809 B1 | 3/2003 | Thomas et al. | |
| 6,622,032 B1 | 9/2003 | Robinson et al. | |
| 6,684,099 B2 | 1/2004 | Ridder et al. | |
| 6,794,988 B1 | 9/2004 | Weiss et al. | |
| 6,862,091 B2 | 3/2005 | Johnson | |
| 6,983,176 B2 | 1/2006 | Gardner et al. | |
| 7,016,713 B2 | 3/2006 | Gardner et al. | |
| 7,092,832 B2 | 8/2006 | Brown | |
| 7,098,037 B2 | 8/2006 | Haas et al. | |
| 7,173,524 B2 | 2/2007 | Ponziani | |
| 7,202,091 B2 | 4/2007 | Jones et al. | |
| 7,386,152 B2 | 6/2008 | Rowe et al. | |
| 7,446,878 B2 | 11/2008 | Ridder et al. | |
| 7,736,903 B2 | 6/2010 | Lambert et al. | |
| 7,764,982 B2 | 7/2010 | Dalke et al. | |
| 7,848,605 B2 | 12/2010 | Ridder et al. | |
| 7,993,281 B2 | 8/2011 | Stock et al. | |
| 8,306,595 B2 | 11/2012 | Osaki et al. | |
| 8,469,134 B2 | 6/2013 | Osaki et al. | |
| 8,605,959 B2 | 12/2013 | Kangas | |
| 8,773,390 B1 | 7/2014 | Clark | |
| 9,068,885 B2 | 6/2015 | Kluczynski et al. | |
| 9,163,718 B2 | 10/2015 | Nelson | |
| 9,823,237 B2 | 11/2017 | Martin et al. | |
| 2003/0039299 A1* | 2/2003 | Horovitz | G01N 27/123 374/141 |
| 2003/0048000 A1 | 3/2003 | Harter | |
| 2003/0085284 A1 | 5/2003 | Bremer et al. | |
| 2004/0093957 A1 | 5/2004 | Buess et al. | |
| 2004/0260194 A1* | 12/2004 | Bayer | G01N 33/4972 600/529 |
| 2005/0241871 A1 | 11/2005 | Stewart et al. | |
| 2006/0058697 A1 | 3/2006 | Mochizuki et al. | |
| 2006/0153740 A1* | 7/2006 | Sultan | G01N 33/4972 422/88 |
| 2006/0167349 A1 | 7/2006 | Gardner et al. | |
| 2006/0206034 A1 | 9/2006 | Stock et al. | |
| 2006/0210120 A1 | 9/2006 | Rowe et al. | |
| 2006/0253711 A1 | 11/2006 | Kallmann | |
| 2007/0077176 A1 | 4/2007 | Lambert et al. | |
| 2007/0142720 A1 | 6/2007 | Ridder et al. | |
| 2007/0144812 A1 | 6/2007 | Stewart et al. | |
| 2007/0245801 A1 | 10/2007 | Stock | |
| 2008/0006077 A1 | 1/2008 | Crabtree et al. | |
| 2008/0045806 A1 | 2/2008 | Keppler | |
| 2008/0061238 A1 | 3/2008 | Hok et al. | |
| 2008/0107309 A1 | 5/2008 | Carni | |
| 2008/0171947 A1 | 7/2008 | Ruffert | |
| 2008/0228098 A1 | 9/2008 | Popov et al. | |
| 2008/0252412 A1 | 10/2008 | Larsson et al. | |
| 2008/0319286 A1 | 12/2008 | Ridder et al. | |
| 2009/0007634 A1 | 1/2009 | Mitchell | |
| 2009/0039267 A1 | 2/2009 | Arndt et al. | |
| 2009/0248260 A1 | 10/2009 | Flanagan | |
| 2009/0293589 A1 | 12/2009 | Freund et al. | |
| 2010/0010325 A1 | 1/2010 | Ridder et al. | |
| 2010/0028210 A1 | 2/2010 | Ozaki et al. | |
| 2010/0031718 A1 | 2/2010 | Heil | |
| 2010/0036592 A1 | 2/2010 | Osaki et al. | |
| 2010/0188232 A1 | 7/2010 | Lambert et al. | |
| 2010/0327167 A1 | 12/2010 | Koop et al. | |
| 2011/0178420 A1 | 7/2011 | Ridder et al. | |
| 2011/0283770 A1 | 11/2011 | Hok | |
| 2011/0302992 A1 | 12/2011 | Robbins et al. | |
| 2011/0308297 A1 | 12/2011 | Tsuzuki et al. | |
| 2011/0309932 A1 | 12/2011 | Arringdale et al. | |
| 2013/0110311 A1 | 5/2013 | Ver Steeg | |
| 2014/0002237 A1 | 1/2014 | Infante et al. | |
| 2014/0156149 A1 | 6/2014 | Feit | |
| 2014/0260537 A1 | 9/2014 | Nash | |
| 2014/0318293 A1 | 10/2014 | Nelson | |
| 2015/0066238 A1 | 3/2015 | Todd | |
| 2015/0219620 A1 | 8/2015 | Hok | |
| 2015/0233897 A1 | 8/2015 | Hok | |
| 2017/0274768 A1 | 9/2017 | Hök et al. | |

FOREIGN PATENT DOCUMENTS

| | | |
|---|---|---|
| CN | 101334399 A | 12/2008 |
| CN | 101631497 | 1/2010 |
| CN | 102316801 A | 1/2012 |
| DE | 41275999 A1 | 2/1993 |
| DE | 198 11 872 | 8/1999 |
| DE | 199 38 064 | 8/2000 |
| DE | 101 57 907 | 6/2003 |
| DE | 102006018970 B3 | 5/2007 |
| DE | 10 2011 106410 | 8/2012 |
| EP | 0752584 A2 | 1/1997 |
| EP | 0 791 899 | 8/1997 |
| EP | 1441212 A1 | 7/2004 |
| EP | 1688741 | 8/2006 |
| EP | 1688741 A2 | 8/2006 |
| GB | 2431470 | 4/2007 |
| GB | 2442980 | 4/2008 |
| JP | 11-104112 | 4/1999 |
| JP | 2004-245799 | 9/2004 |
| JP | 2005-157599 | 6/2005 |
| JP | 2006-98058 | 4/2006 |

(56) References Cited

FOREIGN PATENT DOCUMENTS

| | | |
|---|---|---|
| JP | 2007-147592 | 6/2007 |
| JP | 2008-253455 | 10/2008 |
| JP | 2008-291710 | 12/2008 |
| JP | 2008-302915 | 12/2008 |
| JP | 2008-308037 | 12/2008 |
| JP | 2011-153956 | 8/2011 |
| JP | 2012-198648 | 10/2012 |
| SE | 536782 | 8/2014 |
| SE | 536784 | 8/2014 |
| WO | WO 92/22813 | 12/1992 |
| WO | WO 95/26889 | 10/1996 |
| WO | WO97/000443 | 1/1997 |
| WO | WO 1998/020346 | 5/1998 |
| WO | WO 01/08554 | 2/2001 |
| WO | WO-2004090786 | 10/2004 |
| WO | WO 2007/046745 | 4/2007 |
| WO | WO 2008/108714 | 9/2008 |
| WO | WO-2010085716 | 7/2010 |
| WO | WO 2010/093317 | 8/2010 |
| WO | WO12/064252 | 5/2012 |
| WO | WO 2013/081519 | 6/2013 |
| WO | WO 2014/031071 | 2/2014 |
| WO | WO 2014/031072 | 2/2014 |
| WO | WO 2016/195803 | 12/2016 |
| WO | WO 2017/164953 | 9/2017 |

OTHER PUBLICATIONS

Extended European Search Report EP 13 83 0956 dated Jul. 13, 2015.
Extended European Search Report EP 13 83 1692 dated Jul. 13, 2015.
Giebel, Brian M., Thesis and Dissertation, "Advancement and Application of Gas Chromatography Isotope Ratio Mass Spectrometry Techniques for Atmospheric Trace Gas Analysis," Published 2011, 252 total pages.
International Search Report dated Jan. 31, 2014 for PCT/SE2013/050990.
Talbert, Bruce, et al., "A Study of Regulators for Delivering Gases Containing Low Concentrations of Hydrogen Sulfide," LCGC North America, 22(6):562, 564, 567-568 (2004).
Dhokalia et al., Resting End-Tidal CO2 Association With Age, Gender, and Personailty, Psychosomatic Medicine, vol. 60, 1998, pp. 33-37.
Lambert et al., Passive Sensing of Driver Intoxication, SAE Technical Paper 2006-01-1321, 2006, SAE International.
International Search Report dated Feb. 3, 2014 for PCT/SE2013/050991.

\* cited by examiner

HIGHLY ACCURATE BREATH TEST SYSTEM

CROSS-REFERENCE TO RELATED APPLICATIONS

This application is a national stage application under 35 U.S.C. § 371 of International Application No. PCT/SE013/050990, filed Aug. 23, 2013, which claims priority from Swedish Application 1250953-5, filed Aug. 24, 2012. The contents and disclosures of each of those applications are incorporated by reference herein in their entity. International Application No. PCT/SE2013/050990 was published under PCT Article 21(2) in English.

This invention is concerned with a system for sensing the presence/concentration of substances, such as ethyl alcohol, within the expired breath of a person.

BACKGROUND OF THE INVENTION

Breath alcohol concentration (BrAC) is related to blood alcohol concentration (BAC) by the approximate relation BrAC[mg/1]=0.5*BAC[mg/g]. Other substances will have different coefficients.

Supervised breath tests according to the state of the art are being performed by the police in order to prevent drunk driving. For the same purpose, unsupervised tests using alcolocks in vehicles are also being increasingly used. Sensor technologies include catalytic semiconductors, fuel cells and infrared spectroscopy. Performance with respect to accuracy, specificity, environmental immunity, and response time, is highly variable between different devices available on the market. Devices for breath test include sensor elements providing a signal representing BrAC after taking a deep breath, and emptying the airways via a tight-fitting mouthpiece, which for hygienic reasons has to be a separate, disposable item. In order to ensure a correct determination, the test person is required to deliver a forced expiration at almost full vital capacity. This requires substantial time and effort, especially for persons with limited capacity. The handling of mouthpieces is time-consuming and represents an undesired source of error due to water condensation. The accuracy of the determination represents an increasing challenge, especially when the determination is related to legal limits. Highly accurate breath analyzers for evidential purposes are commercially available, but they are expensive. There is a strong market pull for mass produced devices capable of accurate and reliable breath testing at low cost, and minimum effort for the person to be tested.

The basic techniques of breath analysis were developed during the second half of the 20th century. More recently, a movement towards less obtrusive means for breath test has been noted. Olsson et al (WO 98/20346) disclosed a system solution in which accurate measurements could be performed without a mouthpiece using water vapor as a tracer gas. Lopez (U.S. Pat. No. 5,458,853) reported another approach, using ultrasound to correct for the dependence on distance between the device and the user's mouth. Hök et al (GB 2431470) disclosed a system solution using carbon dioxide ($CO_2$) as a tracer gas, combined with a simple algorithm for correction of a diluted breath sample. Still another approach was reported by Lambert et al (SAE World Congress Apr. 3-6, 2006). The air within a vehicle cabin was monitored, and an alcohol adsorbing material was used to accumulate the sample to enhance resolution. Again, $CO_2$ was used as a tracer gas.

SUMMARY OF THE INVENTION

The object of the present invention is to increase the accuracy of breath test systems. The invention is based on a few critical elements which in combination will provide the necessary characteristics. First, there is a sensor unit providing a signal corresponding to the alcohol concentration of air flowing through a predefined inlet area, by which is meant one or several openings allowing air to be continuously flowing from the inlet area to the sensor unit. Second, an analyzer is included for the determination of breath alcohol concentration of said person based on the sensor signal. A third element is means for controlling the interruption of the air flow at a point in time coinciding with the detection of a breath sample, allowing the sensor unit to be purged after a short period of time upon completion of the determination. In one embodiment of the system according to the invention, means for generating or assisting air flow, e.g. a fan or pump is also included in the system. In this embodiment, flow interruption is accomplished by actively turning off the fan upon detection of a breath, and automatic purging after the determination. In another embodiment without a fan or pump, flow interruption is accomplished by means of a flap valve. These embodiments can, of course, also be used in combination.

The combined function of the basic elements is necessary and sufficient for obtaining the required accuracy. One improvement of the present invention is that the sampled air will be trapped in the sensor unit by interrupting the air flow. The breath analysis will therefore be performed at higher concentration than would otherwise be the case. This also leads to improved accuracy.

By interrupting the air flow, it is possible to prolong the measurement time, and perform signal averaging. Random errors are then reduced by a factor $\sqrt{(T_{av}/T_s)}$, where $T_{av}$ is the averaging time, and $T_s$ is the time between two signal samples. For example, with $T_s=0.2$ seconds, and $T_{av}=2$ seconds, the accuracy will be improved by $\sqrt{10}=3.16$.

The benefits of interrupting the air flow will be even more dramatic with respect to flow-related systematic errors, which are manifested by false readings. Influence of air flow exists both as a direct effect, and indirectly via temperature gradients. These errors will be highly depending on the actual components used, and are significant especially at low concentrations.

The flow interruption should be only temporary, during determination of breath alcohol concentration or measurement of background concentration. Otherwise air flow through the measurement cell should be maintained whenever the system is active, allowing variations in ambient gas concentrations to be continuously monitored. Interruption also includes temporary reduction of the air flow to a significantly lower magnitude, without necessarily stopping it completely.

The present invention allows breath tests to be performed in a variety of circumstances which have hitherto been inaccessible. The improved accuracy, usability and possibility of vehicle integration may be an important step towards preventing drunk driving on a much larger scale than with products available at the present. This is believed necessary to reduce the high mortality of alcohol related traffic accidents. Other promising application areas are sobriety control of staff with critical tasks, and of audience arriving at an arena. It may also be used in various self test scenarios, e.g. in the treatment of alcoholics. The possibility of unobtrusive breath tests is expected to become important for diagnostic purposes in emergency medicine. For this purpose, a large number of volatile substances are of interest in addition to ethyl alcohol.

To meet the object the invention in a first aspect provides a system for breath test of a person as defined in claim 1. It includes a sensor unit configured to sense the presence/concentration of a volatile substance, present in air flowing through a predefined inlet area and generating a signal corresponding to the concentration of said substance, an analyzer for the determination of the concentration of said substance in the breath of said person, the determination being based on said signal corresponding to the substance concentration, and means for the temporary interruption of said air flow at a point in time coinciding with the detection of a breath.

In a second aspect it provides a method of performing a breath test of a person defined in claim 12. It comprises the steps of providing a test system comprising a sensor configured to sense the presence/concentration, of a volatile substance, present in air from the breath of said test person flowing through a predefined inlet area (4) and generating a signal corresponding to the concentration of said substance, interrupting the flow through said predefined area for a limited period of time, and detecting the concentration of said substance during said interruption

BRIEF DESCRIPTION OF THE DRAWINGS

The invention will now be described below with reference to the drawings in which.

DETAILED DESCRIPTION

Figure 1:
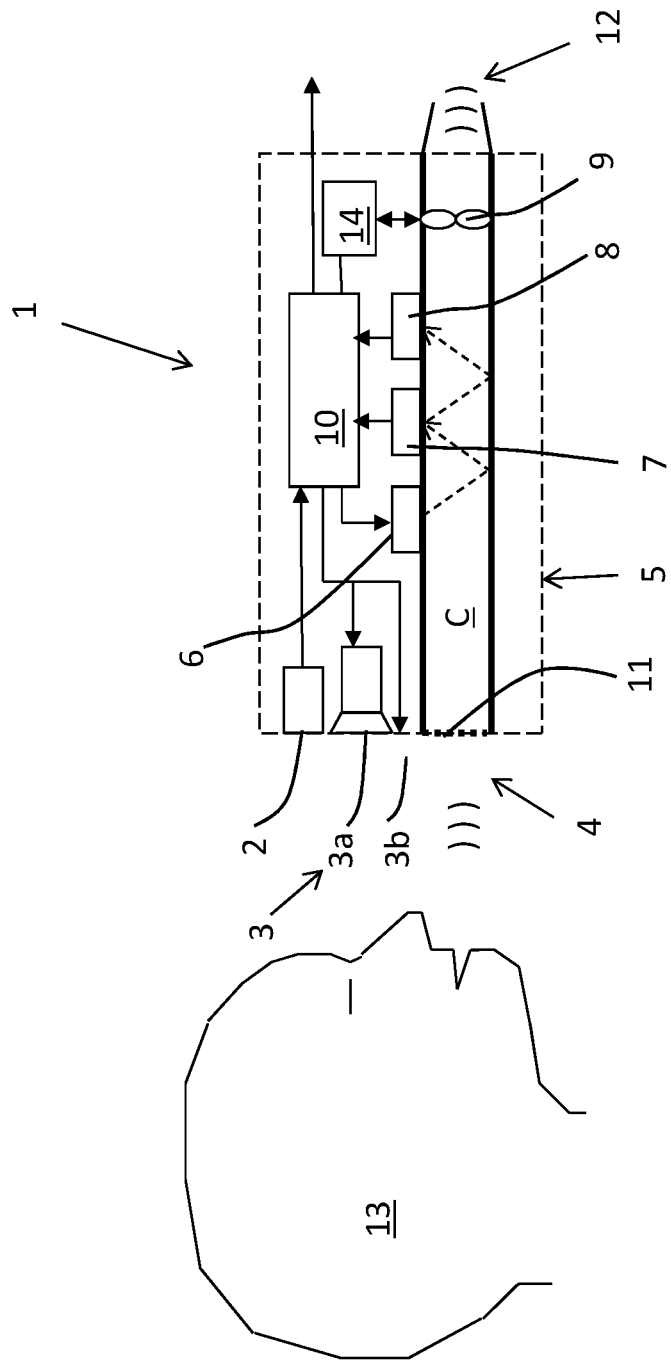
FIG. 1 shows a schematic drawing of the system according to one embodiment.

FIG. 1 shows a schematic drawing (not to scale) of one embodiment of the system 1 according to the invention.

It comprises a sensor unit 5 including a compartment C which forms a passage for breath air that is to be analyzed, a source 6 of IR light, i.e. an IR emitter, and a first sensor 8 capable of detecting a volatile substance, e.g. ethanol, a second sensor 7 capable of detecting e.g. $CO_2$, and suitably a fan or a pump 9, driven by a motor.

The system suitably also comprises a presence detector 2 for detecting that a test person is in the vicinity of the system, and also preferably an audiovisual unit 3 comprising a display unit 3b and a loudspeaker 3a.

The system also comprises an analyzer 10, which preferably includes a general purpose digital microcontroller with capacity to execute signal algorithms, and means 14 for bidirectional control of current drive pulses to the motor driving the fan or pump.

A test person 13 is shown positioned in the vicinity of an inlet area 4 of the sensor unit 5, equipped with a sensor element 8 generating a signal corresponding to the ethyl alcohol concentration of the air flowing through the inlet area 4. Air flow generating means through the sensor unit 5 is provided by a fan or pump 9. The inlet area 4 constitutes one or several openings, into which air can be freely flowing, driven by the fan 9. Preferably, a particle filter 11 e.g. made from porous material is included in the inlet area 4. This prevents particles and aerosols from contaminating the sensor unit 5 while not impeding the air flow to any significant degree. There is also an outlet area 12 from which the air flow is returned into the ambient. In one embodiment of the invention, the outlet area includes a flap valve indicated in FIG. 1 by two hinged thin walls, allowing air flow in one direction only. To remain open, it is necessary to maintain a horizontal pressure gradient (direction referred to FIG. 1) across the thin walls. If such a gradient is too small, absent or reversed, the hinged wall will fall back into a vertical position closing the outlet area 12. The exact closure point of the flap valve is depending on the properties of the hinges and walls, and may be adjusted to any particular requirement. There are also options to a flap valve, such as an electromagnetically controlled valve.

When the person 13 is directing expiratory air towards the inlet area 4 from a distance not exceeding 50 cm, the air flowing through the sensor unit 5 will consist of a mixture of ambient and expiratory air from the person 13.

The present system is capable of interaction with the person 13 during a short moment of time. The apparatus for this includes means for registration 2 of the presence of a person 13 at a position in the vicinity of the inlet area 4, and an audiovisual unit 3. The implementation of the means of registration 2 is highly depending on the actual application and could include a microswitch indicating door opening/closure, microphone, camera, contactless detector using ultrasound or infrared radiation, force sensor responding to the weight of the person. It may include means for identification of the person by voice control, image analysis, bar-code reading, or biometric analysis. The audiovisual unit 3 preferably includes a loudspeaker 3a and a display 3b. The loudspeaker 3a may generate artificial speech or symbolic sound tracks, and the display 3b may convey text, images, icons or other symbols.

Preferably, the audiovisual unit 3 is located in close vicinity to the inlet area 4, in order to direct the person's 13 attention to this area. It is capable of calling for the immediate attention of the person 13 upon presence registration or at some later instant. It is also capable of conveying an instruction, even a detailed one, in the case that the person 13 may need one.

As a consequence of mixing between ambient and expiratory air, the signal generated by the sensor element 8 will be diminished by a factor corresponding to the dilution of the expiratory air. Therefore, another sensor element 7 is included in addition to the element 8, for measuring the concentration of a tracer gas, e.g. carbon dioxide ($CO_2$) or water vapor. Since the tracer gas concentration is approximately constant when leaving the airways, it is possible to obtain a fair approximation of the degree of dilution of the air entering the sensor unit 5. Another option for a tracer signal besides $CO_2$ and $H_2O$ is temperature. The temperature of expiratory air is almost the same as body temperature as it leaves the mouth or nose but will get closer to ambient upon mixing.

The sensor elements 7 and 8 constitute the receiver ends of a measurement cell for infrared (IR) transmission measurement. From an infrared emitter 6, preferably a black-body radiating element, a beam of broadband infrared radiation is illuminating the cell, and eventually after multiple reflections it will reach the elements 7, and 8. Preferably, the emitter 6 is modulated at a frequency, e.g. 5 Hz, above the frequency band of typical signals. Each of the sensor elements 7 and 8 include thermopile detectors of infrared radiation with bandpass interference filters tuned to the absorption peak of the substance to be detected. The element 8 includes a filter with the pass band within the interval 9.1-9.9 µm for ethyl alcohol, and the element 7 the filter in the interval 4.2-4.3 µm in the case of $CO_2$ as tracer gas.

Water vapor, an alternative tracer gas, has strong absorption in the wavelength intervals 2.5-2.8 μm and 5.7-6.9 μm. Other combinations of gases and filter characteristics are possible. Acetone, acetaldehyde, methyl alcohol, carbon monoxide, methane, ethane, propane, pentane, hexane, heptane, octane, isoprene, ammonia, hydrogen sulfide, methyl mercaptan, ethyl acetate, dimethyl ether, diethyl ether, benzene, toluene, methyl ethyl ketone, and methyl isobutyl ketone are examples of volatile substances that may be of interest from a diagnostic or toxicological perspective.

The optical path from the IR emitter 6 to the detectors 7, and 8 may depend on the concentration range and the absorption coefficients of the actual substances. $CO_2$ has strong absorption and high concentration in expiratory air which calls for a short optical path, 10-25 mm. For alcohol detection below the legal concentration limits, path lengths of more than 0.5 m may be necessary. By folding the optical path using multiple reflections, the length/width/height of the sensor unit 5 can still be kept smaller than 70/30/15 mm.

The sensor unit 5 responds almost instantaneously, i e within a fraction of a second, to concentration variations occurring at the inlet area 4. This is partly due to the small distance between the inlet area 4 and the sensor unit 5, typically 10-20 mm, its small inner volume, typically 20-60 ml, and the air volume flow, typically 100-200 ml/sec, generated by the fan 9, and the air flow velocity generated by the fan 9. It is also due to the relatively fast modulation frequency of the infrared emitter. The signal information extracted from the sensor elements 7 and 8 is represented as the amplitude of the modulation frequency.

In order to meet requirements on electromagnetic emission and immunity, the system according to the invention includes capacitive and inductive electronic elements for protective purposes. In addition, the elements 7 and 8 and their associated analog input stages are preferably equipped with differential preamplifiers in order to suppress the influence of common mode interference.

The signals from the sensor elements 7, 8 are brought to an analyzer 10, which preferably includes a general purpose digital microcontroller with capacity to execute signal algorithms, and also controlling the audiovisual unit 3, IR emitter 6, fan 9. Signal conversion between different formats, including analog signals, can be managed by the microcontroller 10, which will also be capable of communicating with external units, e.g. an actuator unit for taking action or counteraction depending on the result of the breath test. Electric power for the system 1 can either be obtained from a battery or from an external power source. The system 1 can be designed as a stand-alone handheld unit, or as an integrated part of other inventories, e.g. a vehicle compartment or entrance of building or workplace. Preferably, the inlet area 4 includes means for protection of the sensor unit 5, e.g. a lid which is closed when the system 1 is inactive. The flap valve 12 is capable of fulfilling this function.

Preferably, the moving parts of the fan 9 have a small mass, typically less than 1.5 gram, in order to have minimum start and stopping time. The fan 9 preferably also includes a brushless DC motor, and means 14 for bidirectional control of current drive pulses to the motor, making use of the fact that the electromagnetic effect is reversible between motor and generator function, designated in FIG. 1 by the bidirectional arrow between the fan 9 and control circuit 14, available from several suppliers, e.g. Texas Instruments Inc., USA. By this control function it is possible, both to start/stop the fan 9 very quickly, and to run it at different speeds. Its feedback loop may also include a flow sensor, measuring the actual air flow. Start and stopping times can be kept at a minimum by the control and drive circuit 14.

In the off mode, the fan 9 represents a significant flow constriction, which effectively traps the air inside the sensor unit 5. The cross section area of the fan 9 allowing free passage of air is considerably typically less than a fourth of the inlet area 4. This constriction constitutes a flow resistance preventing undesired venting of the sensor unit 5 during the time of measurement.

The system according to the invention is preferably confined in a box to be wall-mounted in such a way that the means for registration 2, audiovisual unit 3, and inlet area 4, are located on one side of the box and thereby accessible through a hole in the wall.

The air flow control means 10, 14 may also be used for other purposes than improving accuracy. It may also be used during startup of the system for improving the stability of the sensor unit (5), and minimizing the startup time. Another use is to monitor long-term degradation of bearings or other sensitive parts.

Figure 2:
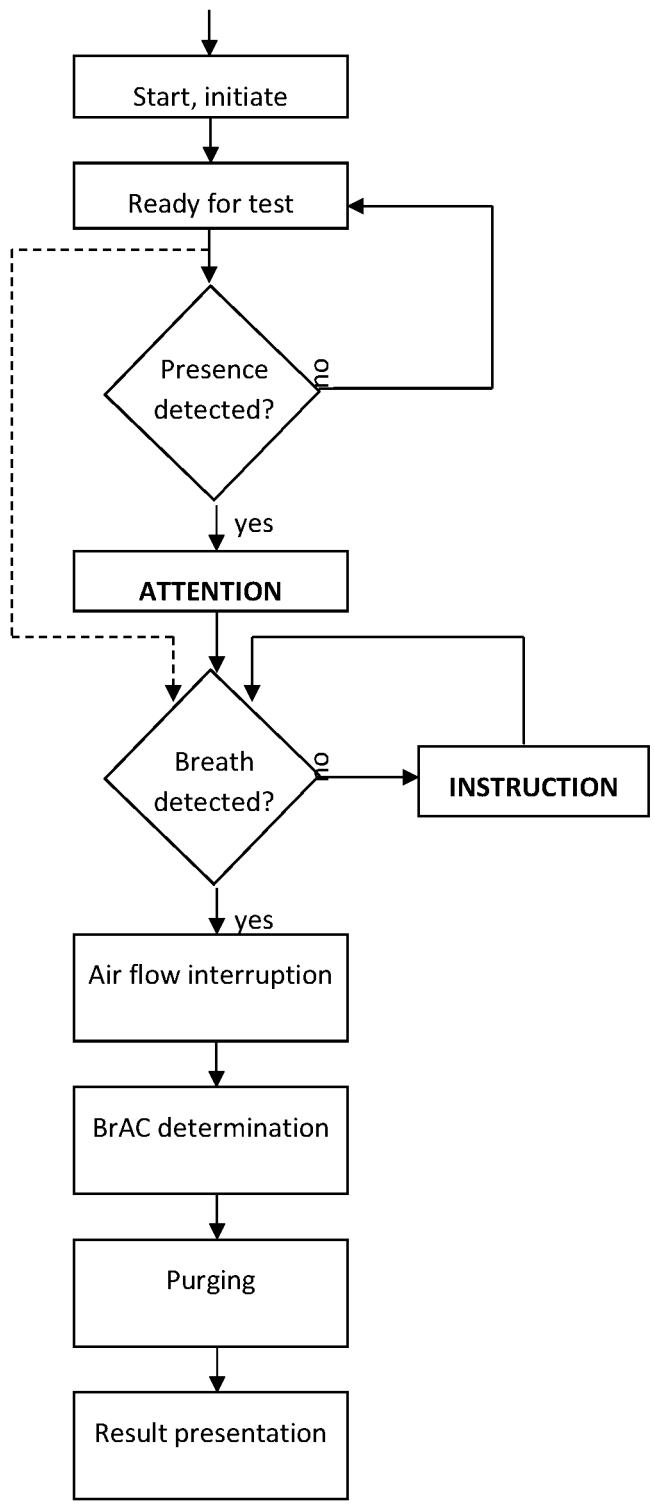
FIG. 2 shows a flow graph of the system function.

FIG. 2 shows a flow diagram of the system function according to the invention. The system is started or initiated either manually or automatically, by some external control signal. In the case of a vehicle, the start signal could be unlocking of the vehicle doors. The initiating phase preferably involves some self-testing functions of the system, to make sure that no functional errors have occurred since the previous test occasion. The fan 9 is automatically started, and is running at full or reduced speed until it receives a command to interrupt the flow or run at a different speed. The initiating phase could also include preheating of sensitive components and stabilization of signals.

When the system is ready for test it will remain in a standby condition until the presence of a person within the predefined position is detected. As previously described, detection may or may not involve identification of the person, and could require two-way communication between the person and the system. After or during the presence detection step, the system will call for the person's attention by coordinated flashing light, distinctive and directional sound combined with specific symbol or icon representing the breath test.

An experienced person is then expected to direct expiratory air towards the sensor inlet area, whereas an unexperienced person may require a more or less detailed instruction on how to proceed. Example of instruction provided verbally or as a text message: "Take a deep breath, lean over, open your mouth wide and exhale gently." Alternatively, instructions are provided by still or moving images, graphic symbols or other means. If the criteria for breath detection are not fulfilled after one round of instruction, repeated instructions may be delivered at increasing level of detail.

The criteria for breath detection preferably involve tracer gas detection as previously described. In the case of $CO_2$ as tracer gas, a simple criterion is reaching a threshold $CO_2$ concentration of e.g. 2500 ppm (parts per million), which corresponds to a dilution factor of 20 (alveolar $CO_2$ concentration being approximately 5 vol %, or 50 000 ppm). Additional criteria could be related to the time derivative of the $CO_2$ signal. The simultaneously measured alcohol concentration will in this case have to be multiplied with 20 in order to obtain an estimated breath alcohol concentration. The criteria for breath detection should also include correction for background $CO_2$ concentration, which is typically 400-600 ppm in normal environments. A mathematical expression or algorithm will normally be adequate for defining the criteria, using settable parameters to adapt for variations between different conditions. Such an algorithm can be implemented for execution in real time using standard microcontrollers.

Upon detection of a breath, a command is sent to the fan 9 to interrupt the air flow. The air within the sensor unit will then become trapped, and prolonged measurement may be performed at zero air velocity, which will basically eliminate flow related errors, and allow signal averaging resulting a reduction also of random error, such as noise. The reduction will apply to the determinations of both the substance and the tracer.

In one embodiment of the invention, in the absence of a fan or pump 9, there is no electronic control of the flow interruption. In this embodiment, the air flow is driven by the exhaling person, creating a pressure gradient across the hinged walls of the flap valve 12, and allowing air to pass the outlet area. When the person's exhalation is decreasing or stopping, the flap valve will close, trapping the exhaled air in the sensor unit 5. The exact time of closure is depending on the elasticity of the hinges and walls of the flap valve, and may be adapted to coincide with the detection of a breath, eventually with some delay.

The level of dilution is a measure of the signal quality. High concentration (small dilution factor) provides high confidence of the determination, whereas the influence of interfering factors, such as other nearby persons, will increase with degree of dilution. Preferably, the result of the breath test is presented not only as a concentration but also in terms of an estimated error depending on the dilution factor.

Breath detection may in some applications override the presence detection as symbolized in FIG. 2 by the dotted line short-cutting both the 'attention' and 'instruction' sequences. Another way of expression is to include the tracer gas detection into the 'means of registration'.

Determination of BrAC is performed by another algorithm based on the correlation between the signals from the sensor elements 7 and 8. When the sensor unit 5 is receiving expired air from a person, both sensor elements exhibit concentration peaks which occur almost simultaneously. An average BrAC value is obtained by multiplying a number of measured alcohol concentrations by their respective dilution factors. By signal averaging, the effect of noise and interference is reduced. A small time difference between the $CO_2$ and the alcohol signals due to differences caused by the anatomic dead space or by the design of the sensor unit 5 is also possible to accommodate in the algorithm.

The completion and result of a breath test defined by fulfillment of the criteria for breath detection, is preferably communicated to the person, e.g. using the audiovisual unit 3. The fan 9 is preferably commanded to restart after completed determination in order to purge the sensor unit, preferably at full speed in order to minimize the time before the system is ready for a new breath test. The restart takes place within a limited period of time, such as 1-10 seconds, preferably 1-5 seconds. If no fan or pump 9 is included, the system 1 if handheld may be manually purged by moving it swiftly in the horizontal right to left direction referring to FIG. 1, thereby creating a pressure gradient across the flap valve 12, and allowing fresh ambient air to enter the sensor unit 5.

Basically the same flow diagram applies to the embodiment without a fan or pump, only that purging of the sensor unit 5 is performed manually.

In the flow diagram of FIG. 2, the further steps taken after termination of the actual breath test are not included, since they may be highly depending on the actual application of the breath test. Such steps may involve rule-based decision for controlling action or counteraction based on the determination, e.g. enabling/disabling functions of a vehicle or locking/unlocking of door.

Figure 3:
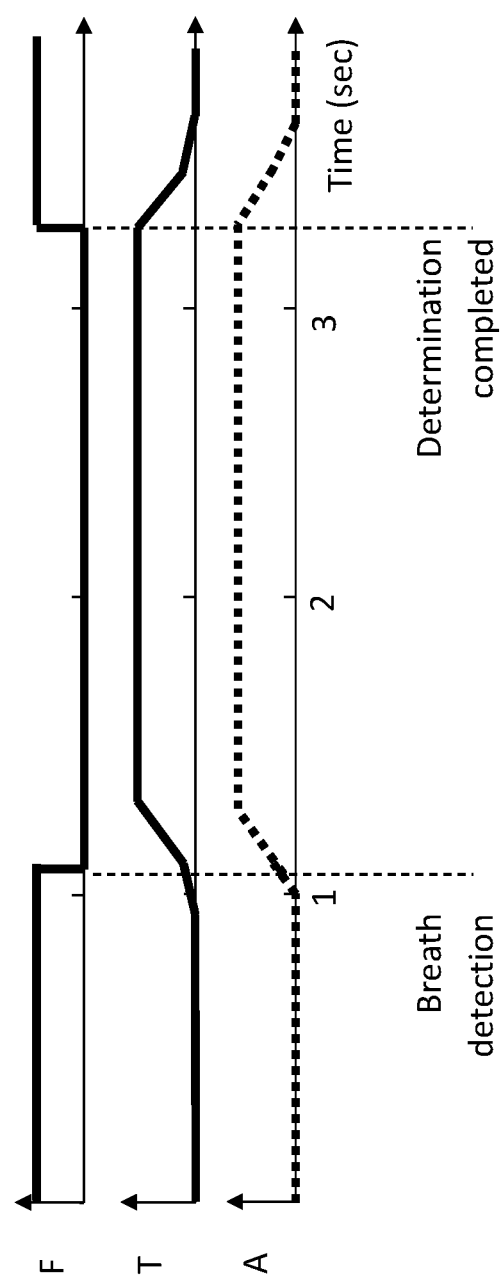
FIG. 3 shows the time sequence of typical breath test performed with the system according to the invention.

FIG. 3 shows a time sequence of a typical breath test performed with the system according to the invention. The signals represented are from top to bottom: 'F' control signal to the fan 9, in which 'high' represents 'on' and 'low' represents 'off', 'T' tracer gas, 'A' alcohol. The time-scale represents a typical sequence of an experienced test person reacting to a request, at time zero, to deliver a breath sample by exhaling towards the inlet area 4. After approximately one second, a tracer signal above a threshold value is noted, and the fan 9 receives a command from the control circuit 14 to interrupt the air flow. After a short delay, the signals of the tracer and the alcohol channels reach a plateau, from which an accurate determination of dilution and BrAC is made, using signal averaging. After completion of the determination, a new command for restart is sent to the fan 9. Upon venting of the sensor unit 5, the signals of both the tracer and alcohol channels return to the original level.

Basically the same time sequence applies to the embodiment without a fan or pump, only that purging of the sensor unit 5 is performed manually.

The invention claimed is:

1. A system for testing the air present in the breath of a person, said system comprising:
    a sensor unit comprising:
        a chamber having an inlet disposed at one end of said chamber and an outlet disposed at the opposite end of said chamber;
        a fan disposed in said inlet for selectively flowing air from a breath of a person through said inlet and into said chamber, wherein said fan is configured to (i) permit air to flow through said inlet when said fan is rotating, and (ii) substantially prevent air from flowing through said inlet when said fan is not rotating;
        a one-way valve disposed in said outlet for (i) permitting air to exit said chamber through said outlet and (ii) preventing air from entering said chamber through said outlet;
        a first sensor element configured to detect the presence and/or concentration of a volatile substance present in said chamber and to generate a signal corresponding to the presence and/or concentration of said volatile substance; and
        a second sensor element configured to detect the presence of a tracer gas in the air in said chamber;
        wherein said sensor unit is configured to stop rotation of said fan upon detection of said tracer gas in said chamber by said second sensor element so as to substantially prevent air from flowing through said inlet; and
    an analyzer configured to determine the concentration of said volatile substance in the breath of the person, the determination being based on said signal from said first sensor element corresponding to the volatile substance concentration.

2. The system according to claim 1, further comprising a means for registration of the presence of a person at a position in the vicinity of said inlet, and an audiovisual unit.

3. The system according to claim 1, wherein said fan is configured to begin rotating after a limited period of time, wherein said limited period of time is 1-10 seconds.

4. The system according to claim 1, wherein said fan includes a brushless DC motor, and means for bidirectional control of current drive pulses to said motor.

5. The system according to claim 1, wherein the free cross sectional area of said fan is less than a fourth of the cross sectional area of said inlet.

6. The system according to claim 1, wherein the mass of moving parts of said fan is less than 1.5 grams.

7. The system according to claim 1, further comprising control means for controlling said fan, including feedback from actual drive elements.

8. The system according to claim 1, wherein said volatile substance is acetone, acetaldehyde, methanol, ethanol, carbon monoxide, methane, ethane, propane, pentane, hexane, heptane, octane, isoprene, ammonia, hydrogen sulfide, methyl mercaptan, ethyl acetate, dimethyl ether, diethyl ether, benzene, toluene, methyl ethyl ketone, or methyl isobutyl ketone or a combination thereof.

9. The system according to claim 1, wherein the distance between said inlet and at least one of said first sensor element and said second sensor element is approximately 10-20 mm.

10. The system according to claim 1, wherein the inner volume of said chamber of said sensor unit is approximately 20-60 ml.

11. The system according to claim 1, wherein air volume flow generated by said fan is approximately 100-200 ml/sec.

12. The system according to claim 2, wherein said system is confined in a box adapted to be wall-mounted in such a way that said means for registration of the presence of a person at a position in the vicinity of said inlet, said audiovisual unit, and said inlet, are located on one side of said box and thereby accessible through a hole in the wall.

13. The method of performing a breath test of a person, comprising the steps of:
providing a system for testing the air present in the breath of a person, said system comprising:
a sensor unit comprising:
a chamber having an inlet disposed at one end of said chamber and an outlet disposed at the opposite end of said chamber;
a fan disposed in said inlet for selectively flowing air from a breath of a person through said inlet and into said chamber, wherein said fan is configured to (i) permit air to flow through said inlet when said fan is rotating, and (ii) substantially prevent air from flowing through said inlet when said fan is not rotating;
a one-way valve disposed in said outlet for (i) permitting air to exit said chamber through said outlet and (ii) preventing air from entering said chamber through said outlet;
a first sensor element configured to detect the presence and/or concentration of a volatile substance present in said chamber and to generate a signal corresponding to the presence and/or concentration of said volatile substance; and
a second sensor element configured to detect the presence of a tracer gas in the air in said chamber;
wherein said sensor unit is configured to stop rotation of said fan upon detection of said tracer gas in said chamber by said second sensor element so as to substantially prevent air from flowing through said inlet; and
an analyzer configured to determine the concentration of said volatile substance in the breath of the person, the determination being based on said signal from said first sensor element corresponding to the volatile substance concentration;
detecting the presence of said tracer gas in said chamber using said second sensor element;
interrupting the flow of air into said chamber by stopping rotation of said fan;
detecting the presence and/or concentration of said volatile substance present in said chamber using said first sensor element;
generating a signal corresponding to the concentration of said volatile substance;
determining the concentration of said volatile substance in the breath of said person using said analyzer, wherein said determination is based on said signal corresponding to the concentration of said volatile substance in said chamber.

* * * * *